(12) United States Patent
Forber

(10) Patent No.: US 9,895,213 B2
(45) Date of Patent: Feb. 20, 2018

(54) VEIN FILTER

(71) Applicant: B. Braun Medical SAS, Boulogne Billancourt (FR)

(72) Inventor: Simon Forber, Boulogne Billancourt (FR)

(73) Assignee: B. BRAUN MEDICAL SAS (FR)

( * ) Notice: Subject to any disclaimer, the term of this patent is extended or adjusted under 35 U.S.C. 154(b) by 159 days.

(21) Appl. No.: 14/646,164

(22) PCT Filed: Nov. 21, 2013

(86) PCT No.: PCT/EP2013/003522
§ 371 (c)(1),
(2) Date: May 20, 2015

(87) PCT Pub. No.: WO2014/079576
PCT Pub. Date: May 30, 2014

(65) Prior Publication Data
US 2015/0305849 A1    Oct. 29, 2015

(30) Foreign Application Priority Data
Nov. 21, 2012  (FR) ...................................... 12 03137

(51) Int. Cl.
A61F 2/01    (2006.01)
A61F 2/86    (2013.01)
A61F 2/82    (2013.01)

(52) U.S. Cl.
CPC .................. *A61F 2/01* (2013.01); *A61F 2/82* (2013.01); *A61F 2/86* (2013.01); *A61F 2002/016* (2013.01)

(58) Field of Classification Search
CPC ...... A61F 2/01; A61F 2/82; A61F 2/86; A61F 2002/016
See application file for complete search history.

(56) References Cited

U.S. PATENT DOCUMENTS 5,968,071 A    10/1999  Chevillon
2005/0055046 A1 *  3/2005  McGuckin, Jr. .......... A61F 2/01
                                             606/200

(Continued)

FOREIGN PATENT DOCUMENTS

EP            0852132       7/1998
WO         2004071343       8/2004

(Continued)

OTHER PUBLICATIONS

International Search Report dated Mar. 7, 2014 for International Application No. PCT/EP2013/003522.

*Primary Examiner* — Jocelin Tanner
(74) *Attorney, Agent, or Firm* — RatnerPrestia

(57) ABSTRACT

A vein filter can switch from a collapsed state to a deployed filtering state and further from this filtering state to an open non-filtering state. The filter includes a plurality of primary filter legs and a plurality of secondary filter legs. The primary filter legs are grouped at one end in a common filter head. One secondary filter leg is connected to each of the primary filter legs in proximity of the filter head. Each secondary filter leg is connected to the adjacent primary leg to which it is not already fixed in proximity of the filter head by a connecting wire attached in the area of the free ends of the legs.

11 Claims, 5 Drawing Sheets

(56) References Cited

U.S. PATENT DOCUMENTS

| | | | | |
|---|---|---|---|---|
| 2006/0025852 A1* | 2/2006 | Armstrong | ....... | A61B 17/12022 623/1.17 |
| 2009/0182371 A1 | 7/2009 | Clausen | | |
| 2010/0042135 A1 | 2/2010 | Shirley | | |
| 2012/0083823 A1* | 4/2012 | Shrivastava | .............. | A61F 2/01 606/200 |

FOREIGN PATENT DOCUMENTS

| | | |
|---|---|---|
| WO | 2006107939 | 10/2006 |
| WO | 2008010197 | 1/2008 |
| WO | 2010082189 | 7/2010 |
| WO | 2012071224 | 5/2012 |

\* cited by examiner

VEIN FILTER

RELATED APPLICATIONS

This application is the U.S. National Phase of International Application No. PCT/EP2013/003522, filed Nov. 21, 2013, which claims the benefit of priority of French Application No. FR 12 03137, filed Nov. 21, 2012. The contents of International Application No. PCT/EP2013/003522 and French Application No. FR 12 03137 are incorporated by reference herein in their entireties.

FIELD

The present invention relates to a convertible vein filter, which can switch from a collapsed state to a deployed filtering state and further on to an open non-filtering state.

BACKGROUND

Vein filters are used for the prevention of pulmonary embolism. A collapsible filter is introduced into the vein through a catheter, usually in the inferior vena cava, to prevent blood clots from travelling to the pulmonary artery. Removable filters are designed to be used temporarily, for example, during surgery, and then be removed. They can also be left permanently in the patient if the patient's condition requires permanent protection. Convertible filters are designed for temporary use and can be transformed into a stent when the filter function is no longer required.

The filters are collapsible so that they can be introduced in their collapsed state into the inner lumen of a catheter and placed in a vein by release from the catheter. The distal end of the catheter is positioned at the desired location of the filter insertion and the latter is then released from the catheter. For this purpose, the filter is usually held in its position relative to the vein by a support device on its proximal end and then the catheter is removed gradually. The collapsed filter expands out of the distal end of the catheter and is deployed into the vein.

A common type of filter is composed of metallic legs that open in an umbrella like manner, grouped on the proximal end at a filter head. In the collapsed state inside the catheter, the legs are under tension and are oriented approximately parallel to each other. Outside of the catheter, because of their elasticity, the legs move apart so that the filter can be deployed into the vein. At least some legs have on their ends barbed hooks to embed the filter in the walls of the blood vessel.

To be convertible, a filter must keep a closed structure after removal of the filter head to transform the filter into a stent configuration. This requires additional connecting wires which connect the filter legs in the stent configuration. The document WO 2006/107939 A1 describes such a filter.

The application of convertible vein filters is however limited by the diameter of the collapsed filter to be introduced into the catheter lumen for insertion of the filter into a vessel. The diameter of the filter head, where all filter legs meet, limits the miniaturization of such filters.

SUMMARY

The goal of this invention is to provide a convertible vein filter with a reduced diameter in the collapsed state.

The goal of the invention is achieved by a vein filter with the characteristics described herein. The vein filter in accordance with the invention can switch from a collapsed state to a deployed filtering state and further from this filtering state to an open non-filtering state. The filter comprises a plurality of primary filter legs and a plurality of secondary filter legs. The primary filter legs are grouped at one end in a common filter head. One secondary filter leg is connected to each of the primary filter legs in proximity of the filter head.

The filter of the invention is characterised in that each secondary filter leg is connected to the adjacent primary leg to which it is not already fixed in proximity of the filter head by a connecting wire attached in the area of the free ends of the legs.

Therefore, the head of the filter in accordance with the invention can have reduced dimensions. Only the primary legs are grouped in the filter head. Their reduced number reduces the diameter of the filter head compared to conventional filters. The diameter of the filter head must normally be greater than the diameter of the filter legs grouped in it, so that the filter head protrudes from the filter legs. The secondary legs can be disposed on the primary legs so that they use the free space under the filter head. The filter diameter does not increase because of the additional secondary legs.

In addition, to obtain a stent configuration in the open state of the filter, it is not necessary to connect all filter legs at their free ends via connecting wires. A secondary leg is already connected to a primary leg in proximity of the head and only requires one connection with the adjacent primary leg to which it is not yet connected. This reduces the number of connecting wires required for the stent configuration by half.

For evenly spacing of the legs in the deployed state, it is advantageous to connect the legs so that they form an angle beyond their connection in proximity of the filter head. In the collapsed state, the legs are stretched so that they extend essentially parallel to one another. The appropriate choice of material allows a secondary filter leg, disposed on a primary leg, to show a bend under the connection area so that the two legs form an angle in the deployed state.

The connecting wires extend advantageously from the free end or a location near the free end of the filter legs in a V shape. Two adjacent filter legs can also be connected with separate wire sections that are connected at their respective free ends. In order to avoid increasing of the total length of the filter the connecting wires extend in most of the cases from the end of the legs towards the filter head.

Such a convertible filter can be converted at any time after implantation into a stent by removing the filter head. The upper ends of the filter legs, which are grouped in the filter head, are released. The filter retains its stability in the blood vessel by virtue of the different connections between primary and secondary filter legs. The upper ends deploy outwards against the vessel wall and the filter remains open in the blood vessel in a stent configuration.

If such a filter is opened by removing the filter head, its legs form a closed structure placed against the blood vessel wall whereby each leg is connected directly or via a connecting wire to the adjacent legs. Compared to a conventional filter, the connecting wires are reduced, by half and thus considerable space is saved.

BRIEF DESCRIPTION OF THE DRAWING FIGURES

A preferred embodiment of the present invention is described in more detail below with reference to the accompanying drawings, of which:

DETAILED DESCRIPTION

Figure 1:
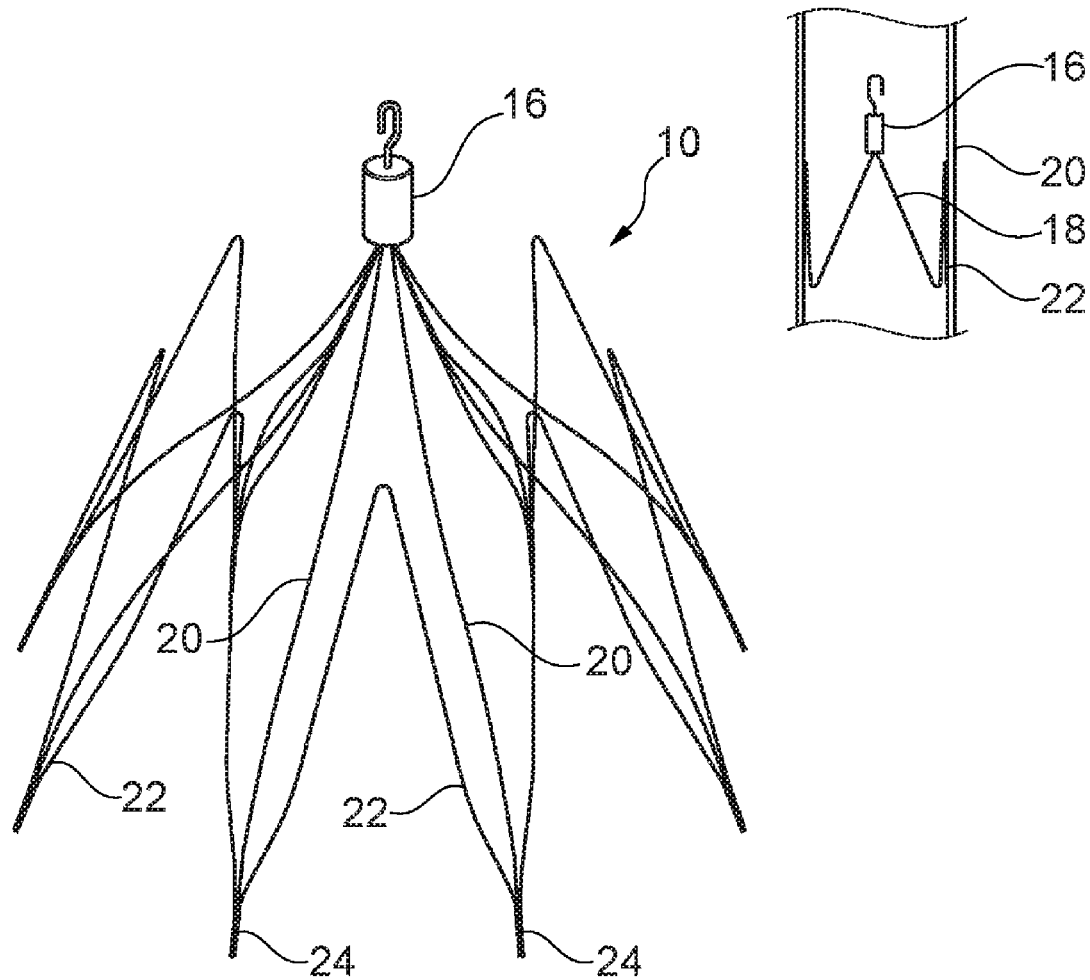
FIG. 1 shows a perspective view of a convertible filter known in the art in the filter configuration as well as a longitudinal section of a filter deployed in a blood vessel.

FIG. 1 shows a perspective view of a convertible filter 10 as known in the art in the filter configuration as well as a longitudinal section of the filter in the blood vessel 18. The filter consists of several filter legs 20, which are grouped in the filter configuration in the filter head 16. The free ends 24 of the filter legs 20 on the opposite of the filter head 16 are interconnected by V-shaped connecting wires 22. If the filter is implanted in a blood vessel 18, the connecting wires 22 rest against the blood vessel wall 18. If positioned correctly, the filter head 16 is approximately in the centre of the blood vessel 18 and the filter legs 20 extend from the filter head 16 outwards towards the blood vessel wall 18, thus fulfilling their filtering function.

Figure 2:
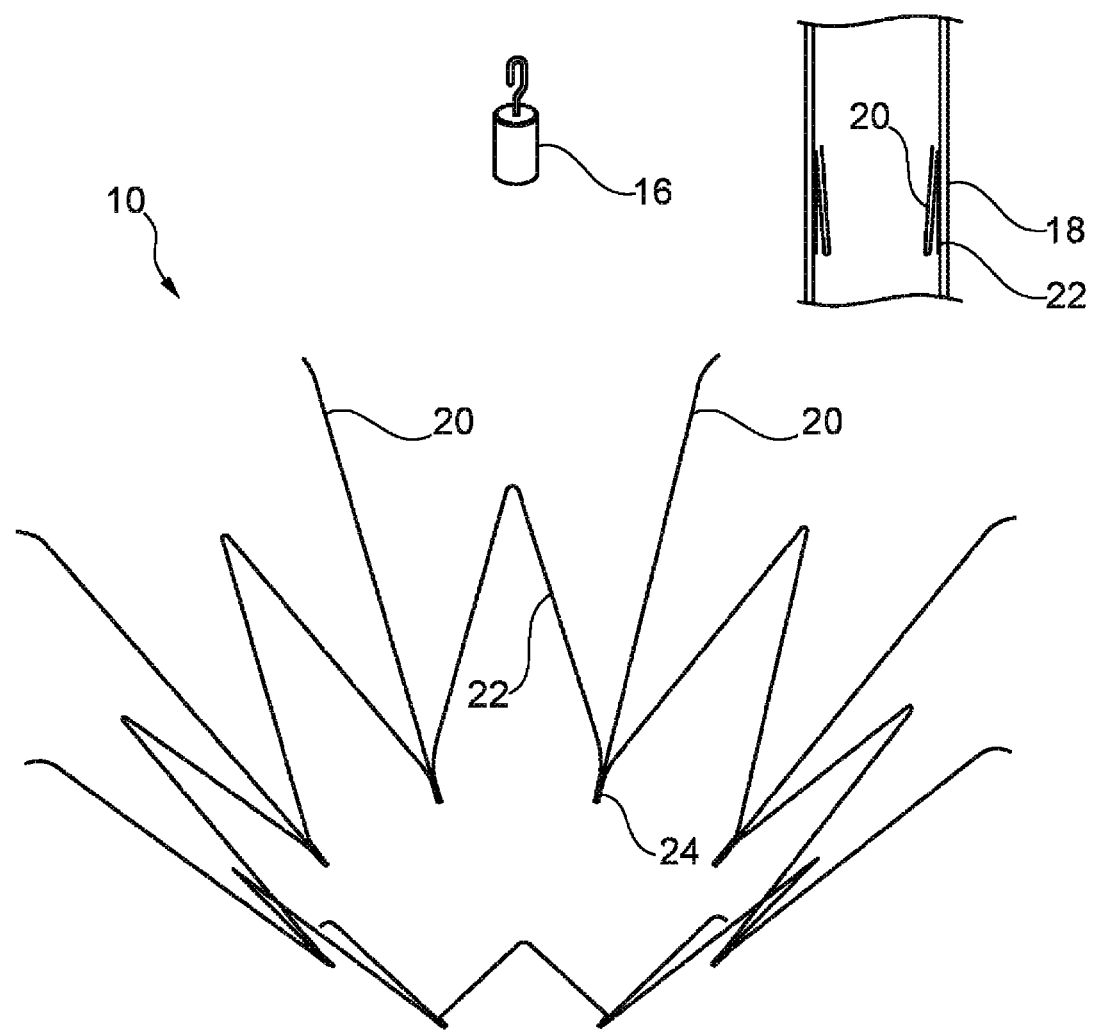
FIG. 2 shows a perspective view of the convertible filter known in the art of FIG. 1 in the stent configuration as well as a longitudinal section of a filter deployed in a blood vessel.

To switch the filter 10 to the stent configuration, the filter head 16, as shown in FIG. 2, is removed. The filter legs 20 tilt outwards against the vessel wall 18 under the effect of the filter tension. By virtue of its connecting wires 22 and despite the removal of the filter head 16, the device maintains a closed ring structure that rests against the vascular wall 18 and acts as a stent.

FIGS. 1 and 2 illustrate that a convertible filter 10 according to the know state of the art in the collapsed state occupies a considerable volume due to the large number of connecting wires 22. Each filter leg 20 requires two arms of a connecting wire 22 so that the cross-section width of such a filter in a catheter is considerably greater than the cross-section width of a conventional non-convertible filter.

Figure 3:
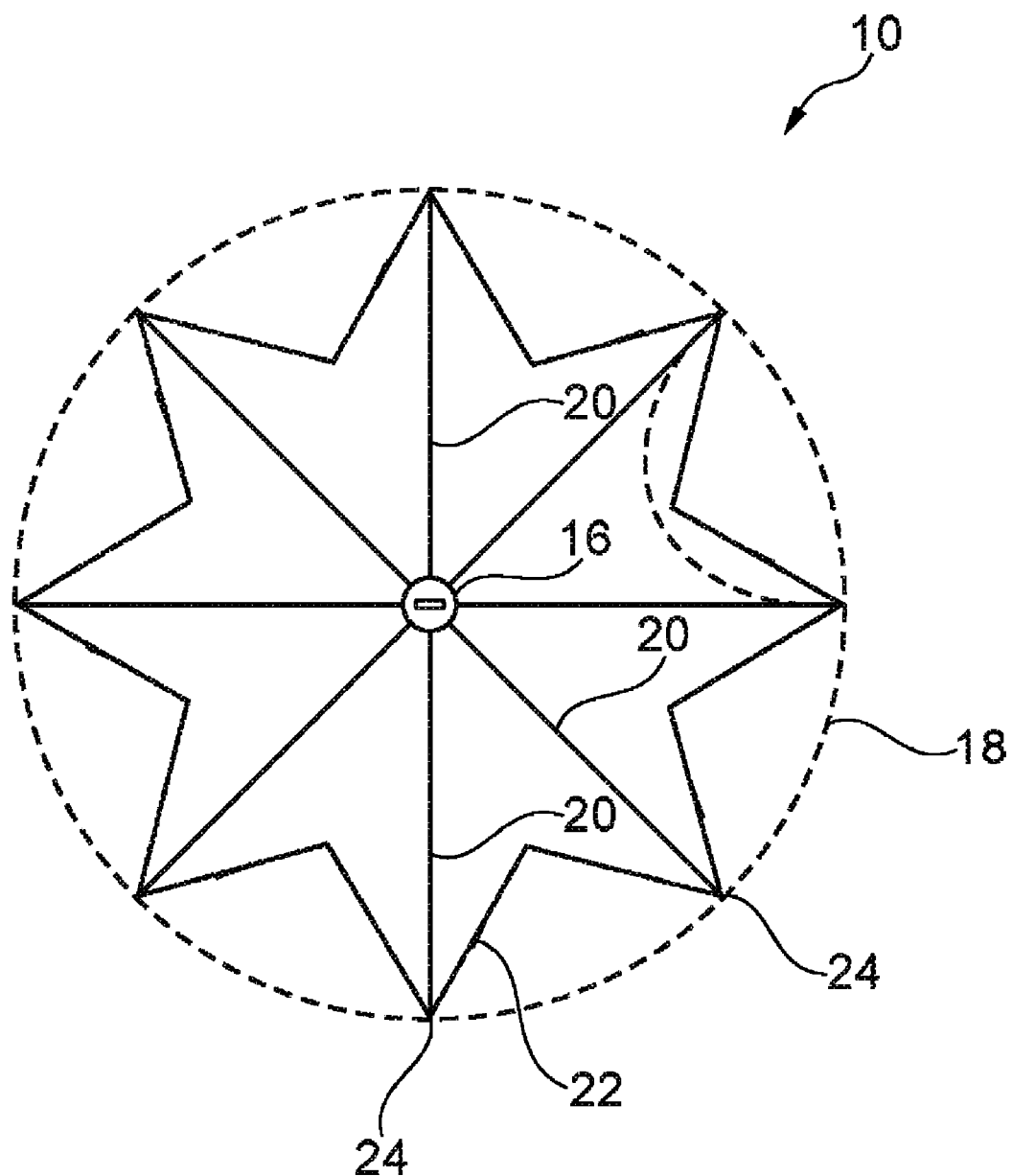
FIG. 3 shows a convertible filter known in the art in the filter configuration in axial projection in a blood vessel.

FIG. 3 illustrates once more a convertible filter 10 as known in the state of the art in axial projection in the filter configuration in a blood vessel 18. The filter head 16, which groups the filter legs 20, is seen clearly. The ends of two adjacent filter legs 24 opposite of the filter head 16 are interconnected by a connecting wire 22. The connecting wires produce a closed structure, which is preserved after removing the filter head 16. The filter can be transformed into a stent configuration.

Figure 4:
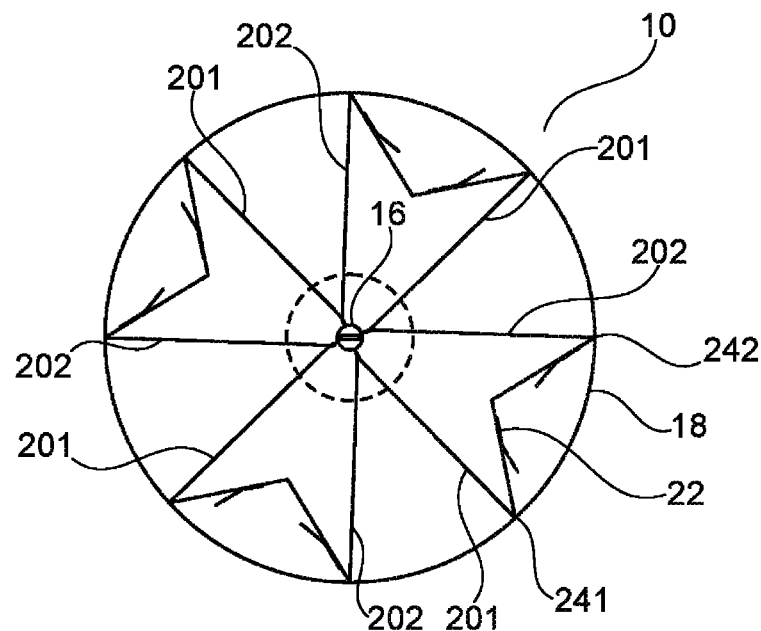
FIG. 4 shows a perspective view of a convertible filter in accordance with the invention in a filter configuration in an axial projection in a blood vessel.
Figure 4A:
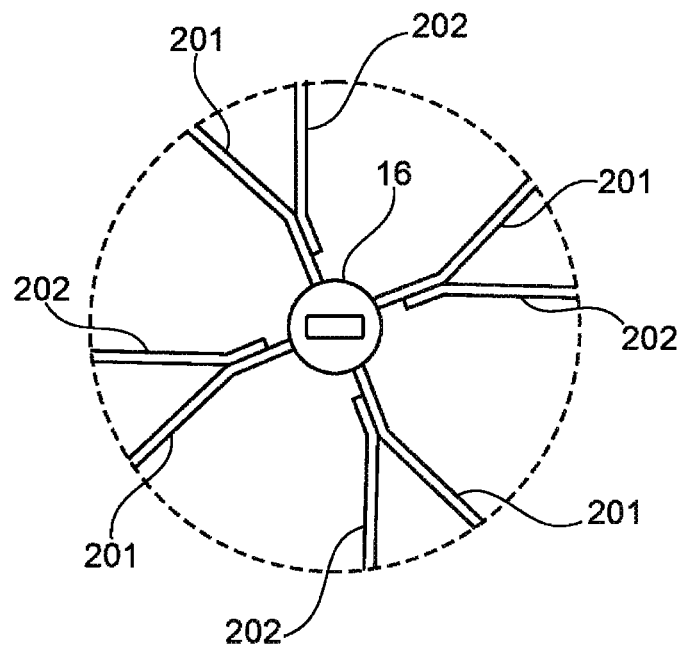
FIG. 4a shows a partial enlargement of the convertible filter of FIG. 4.

FIG. 4 shows a filter 10 according to the invention in an axial projection in a blood vessel 18. FIG. 4a shows a partial enlargement of the area in proximity to the filter head 6. As shown in the figures, the filter 10 consists of four primary filter legs 201 and four secondary filter legs 202 where the primary legs 201 are grouped in the filter head 16. The secondary filter legs 202 are attached to the primary filter legs 201 in proximity to the filter head 16.

The ends 241 of the primary filter legs 201 at the opposite end of the filter head 16 are linked by V-shaped connecting wires 22, to the end 242 of an adjacent secondary leg 202, namely to the secondary leg 202 which is not already attached to the respective primary filter leg in proximity to the filter head 16. Thus, the structure remains closed after removing the filter head 16 and adopts a stent configuration.

The secondary filter legs 202 are shaped such that the primary and the secondary filter legs 201, 202 form beyond their connection area an angle. This ensures an even distribution of legs and consequently a high reliability of such filter.

Figure 5:
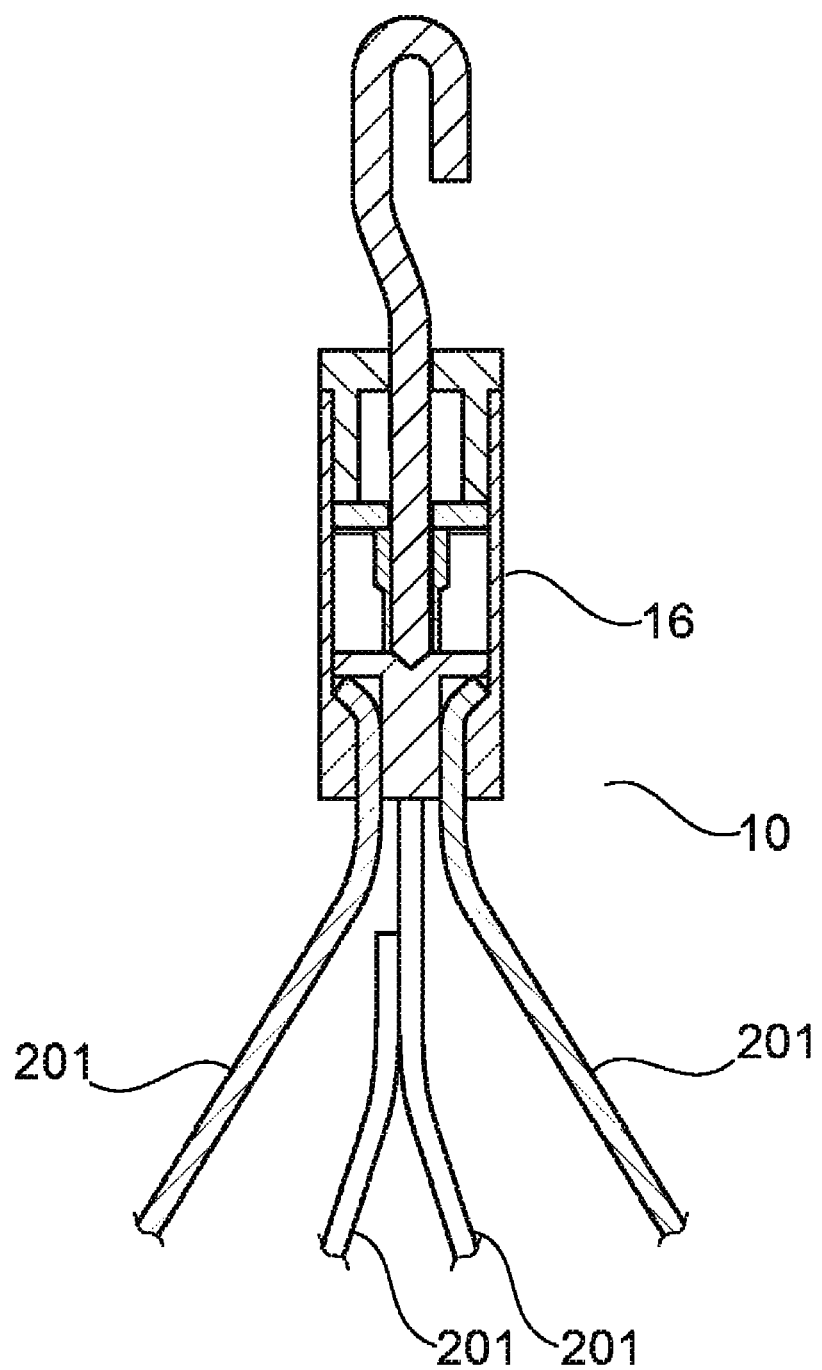
FIG. 5 shows a longitudinal section of the filter head of a convertible filter in accordance with the invention.

FIG. 5 shows a longitudinal section of the filter head region of the convertible filter 10 of FIG. 4. The primary legs 201 are grouped in the filter head 16. It is also shown how a secondary filter leg 202 is directly fixed below the filter head 16 to the primary leg 201. Only the four primary filter legs 16 from the total of eight filter legs meet in the filter head 16. Therefore, the filter head 16 may be smaller than the diameter of a filter head receiving all legs.

The invention claimed is:

1. A vein filter that can switch from a collapsed state to a deployed filtering state and further to an open non-filtering state, the vein filter comprising:
    a filter head;
    a plurality of primary filter legs, each primary filter leg extending from a proximal end to a distal end;
    a plurality of secondary filter legs, each secondary filter leg extending from a proximal end to a distal end; and
    a plurality of connecting wires,
    wherein only the proximal ends of the primary filter legs are grouped in the filter head to allow the filter head to have a reduced size,
    wherein, each secondary filter leg is attached to one of the primary filter legs in proximity to but outside of the filter head, such that each secondary filter leg branches out from one of the primary filter legs outside of the filter head and in a direction extending away from the filter head, and
    wherein, each connecting wire is connected in proximity to the distal end of one of the primary filter legs and in proximity to the distal end of one of the secondary filter legs.

2. The vein filter according to claim 1, wherein the primary and secondary filter legs form an angle beyond their connection in proximity of the filter head.

3. The vein filter according to claim 1, wherein the connecting wires extend towards the filter head in a V shape.

4. The vein filter according to claim 1, wherein each primary filter leg is connected to two secondary filter legs.

5. The vein filter according to claim 1, wherein each secondary filter leg is directly connected to one primary filter leg in proximity of the filter head, and to another primary filter leg by a connecting wire in proximity of the distal ends of the primary filter legs and secondary filter legs.

6. The vein filter according to claim 1, wherein the filter head is detachable from the primary filter legs grouped in the filter head, thus allowing the vein filter to switch from the deployed filtering state to the open non-filtering state.

7. A vein filter according to claim 1, wherein a distance between the distal ends of the secondary filter legs and the filter head is substantially equal to a distance between the distal ends of the primary filter legs and the filter head.

8. A vein filter according to claim 1, wherein both the primary filter legs and the secondary filter legs extend substantially over an entire length of the vein filter and are alternatingly spaced in a circumferential direction.

9. A vein filter that can switch from a collapsed state to a deployed filtering state and further to an open non-filtering state, the vein filter comprising:
- a filter head;
- a plurality of primary filter legs, each primary filter leg extending from a proximal end to a distal end;
- a plurality of secondary filter legs, each secondary filter leg extending from a proximal end to a distal end; and
- a plurality of connecting wires,
- wherein, only the proximal ends of the primary filter legs are grouped in the filter head to allow the filter head to have a reduced size,
- wherein, each secondary filter leg is attached to one of the primary filter legs in proximity to but outside of the filter head, such that each second filter leg branches out from one of the primary filter legs outside of the filter head and in a direction extending away from the filter head, and
- wherein, each connecting wire is attached in proximity to the distal end of one of the primary filter legs and in proximity to the distal end of one of the secondary filter legs, thereby connecting the distal end of each secondary filter leg to only one primary filter leg, which is a primary filter leg other than the primary filter leg from which said secondary filter leg branches out in proximity to the filter head.

10. A vein filter according to claim 9, wherein a distance between the distal ends of the secondary filter legs and the filter head is substantially equal to a distance between the distal ends of the primary filter legs and the filter head.

11. A vein filter according to claim 9, wherein both the primary filter legs and the secondary filter legs extend substantially over an entire length of the vein filter and are alternatingly spaced in a circumferential direction.

* * * * *